United States Patent [19]

Agrawal et al.

[11] Patent Number: 5,026,912

[45] Date of Patent: Jun. 25, 1991

[54] ALKYLATION OF AROMATIC AMINES OVER THERMALLY PRETREATED ZEOLITES

[75] Inventors: Rakesh Agrawal, Allentown; Steven R. Auvil, Macungie, both of Pa.

[73] Assignee: Air Products and Chemicals, Inc., Allentown, Pa.

[21] Appl. No.: 499,925

[22] Filed: Mar. 27, 1990

[51] Int. Cl.$^5$ ............................................ C07C 209/68
[52] U.S. Cl. ..................................... 564/409; 564/307; 560/19; 560/46; 560/47; 560/48; 558/376
[58] Field of Search ................... 564/409, 307; 560/19, 560/46, 47, 48; 558/376

[56] References Cited

U.S. PATENT DOCUMENTS

| | | | |
|---|---|---|---|
| 4,740,620 | 4/1988 | Dixon et al. ........................ | 564/409 |
| 4,760,184 | 7/1988 | Pierantozzi ........................ | 564/409 |
| 4,795,833 | 1/1989 | Mitchell ............................. | 564/409 |
| 4,804,784 | 2/1989 | Weigert ............................. | 564/409 |
| 4,851,579 | 7/1989 | Pierantozzi ........................ | 564/409 |
| 4,876,377 | 10/1989 | Agrawal et al. ................. | 564/409 X |

*Primary Examiner*—Richard L. Raymond
*Attorney, Agent, or Firm*—Keith D. Gourley; James C. Simmons; William F. Marsh

[57] ABSTRACT

A process for selectively producing ortho-alkylated aromatic amines in high selectivity relative to N-alkylated aromatic amines. The process comprises reacting an aromatic amine, having at least one hydrogen atom in a position ortho to the amine functionality, and an olefin under conditions sufficient to effect an alkylation reaction, in the presence of a zeolite catalyst which has been thermally pretreated by heating the catalyst to a temperature greater than about 500° C. for a period ranging from 0.5 to about 10 hours while sweeping an inert gas over the heated catalyst to remove water and ammonia formed during the thermal treatment, and subsequently recovering the alkylated aromatic amine.

15 Claims, No Drawings

000
ALKYLATION OF AROMATIC AMINES OVER THERMALLY PRETREATED ZEOLITES

TECHNICAL FIELD

The present invention relates to an improved process for selectively producing ortho-alkylated aromatic amines in high conversion wherein an aromatic amine, having at least one hydrogen atom in a position ortho to the amine functionality, is contacted with an olefin in the presence of a zeolite catalyst which has been subjected to thermal pretreatment.

BACKGROUND OF THE INVENTION

Processes for preparing ring alkylated aromatic amines by contacting an aromatic amine and a hydrocarbon radical-providing source such as an olefin are widely known. Typical aromatic compounds which undergo such reactions include mononuclear aromatic compounds having one or more hydroxyl, amine or ester substituents. The alkylation of aromatic amines has been carried out in the presence of both homogeneous and heterogeneous catalyst systems.

Ring alkylated aromatic amines, which are readily prepared by the alkylation of aromatic amines, exhibit a variety of uses in commercial applications and are utilized as intermediates in the preparation of substituted isocyanates, herbicidal compositions, dyestuffs and textile auxiliary agents. Recently, aromatic amines have been utilized as chain extenders in the preparation of polyurethane systems.

Representative references which illustrate processes for alkylating aromatic amines include U.S. Pat. No. 4,760,184, assigned to Air Products and Chemicals, Inc., Trexlertown, Pa., which discloses a process for producing ring alkylated aromatic amines wherein an aromatic amine is reacted with an olefin, diolefin or an alcohol in the presence of non-zeolitic molecular sieve catalysts such as crystalline aluminophosphate and crystalline silicoaluminophosphate catalysts. Comparative example 1 discloses the alkylation of aniline with propylene over LZ-Y82, a steam stabilized HY zeolite, which was activated by heating at 95° C. for 4 hours, followed by warming at a rate of 2° C./min. to 400° C. wherein the temperature was held for 4 hours.

U.S. Pat. No. 4,851,579, also assigned to Air Products and Chemicals, Inc., Trexlertown, Pa., discloses a process for alkylating aromatic amines to form ortho-alkylated products wherein an aromatic amine is contacted with an olefin or an alcohol in the presence of an ion-exchanged zeolite in which at least a portion of the exchangeable ion sites has been exchanged with aluminum cations. In a preferred embodiment, the catalyst is heated to about 400° C. prior to the aluminum exchange step to remove residual sodium ions remaining in catalyst exchange sites.

U.S. patent application Ser. No. 370,486, assigned to Air Products and Chemicals, Inc., Trexlertown, Pa., discloses a process for selectively preparing N-alkylated aliphatic amines wherein cyclohexylamine is reacted with an alcohol or diol in the presence of a Y zeolite catalyst which has been impregnated with from 0.01 to about 15 wt % elemental phosphorus based upon the total weight of the impregnated catalyst. In a preferred embodiment, the impregnated Y zeolites are subjected to a thermal treatment wherein the catalyst is heated to temperatures ranging from about ambient to 800° C., in an inert atmosphere for a period of 0.5 to 48 hours. This Application is not prior art assertable against the present invention.

U.S. patent application Ser. No. 370,440, also assigned to Air Products and Chemicals. Inc., Trexlertown, Pa., discloses a process for producing alkylene polyamines wherein an alkanolamine or diol is reacted with ammonia in the presence of a mordenite catalyst which has been impregnated with a phosphorus-containing moiety, under conditions sufficient to effect a condensation reaction. The catalyst may optionally be subjected to a thermal treatment wherein the catalyst is heated to temperatures ranging from 100° to about 800° C., in an inert atmosphere for a period ranging from 0.5 to about 48 hours. This Application is not prior art assertable against the present invention.

Although the prior art discloses a variety of catalytic processes for alkylating aromatic hydrocarbons and aromatic amines, these processes sometimes provide low conversion, poor reaction rate and are incapable of yielding a high ortho to para isomer ratio. A need in the art exists for a process which demonstrates high selectivity and conversion toward formation of ortho-alkylated aromatic amine products while also providing a higher rate of reaction than prior art processes.

BRIEF SUMMARY OF THE INVENTION

The present invention relates to a process for producing an alkylated aromatic amine which comprises reacting an aromatic amine, having at least one hydrogen atom ortho to the amine functionality, and an olefin under conditions sufficient to effect an alkylation reaction, in the presence of a zeolite catalyst which has been thermally pretreated by heating the catalyst to a temperature greater than 600° C. for a period ranging from 0.5 to about 10 hours while sweeping an inert gas over the heated catalyst to remove water and ammonia formed during the thermal treatment, and subsequently recovering the alkylated aromatic amine.

The aromatic amines suitable for practicing the invention are represented by the formula:

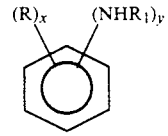

wherein R is a hydrogen atom, a linear or branched alkyl or alkoxy group having from 1 to about 10 carbon atoms, a halogen, phenyl, ester, or a nitrile; $R_1$ is a hydrogen atom or a linear or branched cyclic or acyclic alkyl group having from 1 to about 10 carbon atoms; x is 1 or 2 and y is 1 or 2.

Alkylating agents suitable for use in this invention include linear and branched, acyclic and cyclic olefins having from 2 to about 8 carbon atoms. Representative olefins include ethylene, propylene, butene, isobutylene, isoamylene, cyclohexene, 1-methylcyclohexene and 1-methylcyclopentene.

Suitable zeolites which can be employed include X, Y, K and L zeolites, faujasite, mordenite, offretite, beta, omega, gmelinite, clinoptilolite and the ZSM family selected from ZSM-4, ZSM-5, ZSM-11, ZSM-12, ZSM-21, ZSM-35 and ZSM-38. The catalysts are thermally pretreated prior to effecting the reaction by heating the catalyst to temperatures in excess of about 600° C. for a period ranging from 1 to about 10 hours while sweeping the catalyst bed with dry inert gas in order to remove water and/or ammonia formed during the thermal pretreatment.

The process according to the present invention solves the handling and reactivity problems associated with some commercial homogeneous catalysts currently utilized for the alkylation of aromatic amines. Moreover, the thermally activated zeolites according to the present invention provide improved product selectivity toward the desired ortho alkylated aromatic amines combined with improved reaction rates.

DETAILED DESCRIPTION OF THE INVENTION

The present invention relates to a process for producing ortho-alkylated aromatic amines wherein a zeolite catalyst is subjected to a thermal treatment prior to being placed in contact with the reactants. The claimed process is highly selective toward formation of ortho-alkylated products and provides substantially improved rates of reaction than achieved in current processes known in the art.

The process comprises reacting an aromatic amine and an olefin, under conditions sufficient to effect an alkylation reaction, in the presence of a zeolite catalyst which has been thermally pretreated by heating the catalyst to a temperature greater than 600° C. for a period ranging from 0.5 to about 10 hours while sweeping a dry inert gas over the heated catalyst to remove water and/or ammonia formed during the thermal treatment, and subsequently recovering the alkylated aromatic amine.

The aromatic amines suitable for practicing the process are represented by the formula:

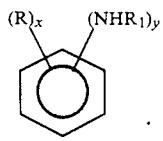

wherein R is a hydrogen atom, a linear or branched cyclic or acyclic alkyl or alkoxy group having from 1 to about 10 carbon atoms, a halogen, phenyl, ester, or a nitrile; $R_1$ is a hydrogen atom or a linear or branched cyclic or acyclic alkyl group having from 1 to about 10 carbon atoms; x is 1 or 2 and y is 1 or 2.

The aromatic amines disclosed herein include both aromatic monoamines and aromatic diamines. The amine functionality may be substituted with a linear or branched alkyl group having from 1 to about 10 carbon atoms. Examples of suitable alkylamino groups include N-methyl, N-ethyl, N-propyl, N-butyl and N-tert-butyl.

The aromatic amines can be substituted with a variety of substituents which are non-reactive with the olefin in the alkylation reaction. Such substituents include linear or branched cyclic and acyclic alkyl groups having from 1 to about 10 carbon atoms. Representative of such alkyl groups are methyl, ethyl, propyl, butyl, isobutyl, tert-butyl, cyclohexyl and methylcyclohexyl. Suitable alkoxy groups include linear and branched cyclic and acyclic alkoxy groups having from 1 to about 10 carbon atoms. Suitable halogens include fluoride, chlorine, bromine and iodine.

Many of the aromatic amines included within the above-mentioned formula have reactive hydrogen atoms situated in positions both ortho and para to the amino group. When the aromatic amine possesses active hydrogen atoms in both the ortho and para ring positions, the process enables the selective production of one isomer in favor of the other. In the case of aromatic amines having reactive hydrogen atoms in the ortho- and para- positions, the para position is more thermodynamically stable.

In typical prior art systems, high conversion of aromatic amine and high selectivity to an ortho-alkylated amine could not often be obtained simultaneously. Consequently, in order to obtain high conversion of aromatic amine, the process conditions were typically adjusted such that higher percentages of the more stable para-isomer were provided. Reactant conversion in many prior art systems was thereby limited to approximately 20% to 30% in order to achieve a high selectivity to the ortho-isomer, e.g., an ortho/para isomer molar ratio of 3 or greater to 1. In contrast, the present invention provides enhanced selectivity toward the desired ortho-alkylated products while maintaining high conversion to product.

Specific examples of aromatic amines suited for alkylation which possess active hydrogen atoms in positions ortho and para to the amino group which are suitable for use in the present process include aniline, toluidine, xylidene, toluenediamine, xylidenediamine, diphenylamine, methylenedianiline, N-ethylaniline, N-propylaniline, n-propylamino-aminotoluene, isobutylaniline, phenylaniline, phenylenediamine and methylbenzylaniline.

Alkylating agents suitable for practicing the invention are linear and branched, cyclic and acyclic olefins having from 2 to about 8 carbon atoms. Representative olefins include ethylene, propylene, butene, isobutylene, isoamylene, cyclohexene, and 1-methylcyclohexene. While alkyl halides such as ethyl chloride, propyl bromide, and the like, can be used as alkylating agents in the present process, they generally are not suited for the ortho-alkylation of aromatic amines because the acid by-product formed during the alkylation reaction tends to diminish selectivity to the ortho product.

In those cases where the aromatic amine can be alkylated in the ortho and para positions, the molar ratio of olefin to aromatic amine influences, to some degree, whether the ring alkylation will occur at a ring position ortho to the amine or para to the amine. Typically, olefin to amine molar ratios for practicing the claimed process range from 1 to about 20 moles olefin per mole of aromatic amine and preferably 2 to about 10 moles olefin per mole of aromatic amine. The utilization of higher mole ratios of olefin to aromatic amine tends to enhance selectivity toward the ortho-alkylated product.

The ortho-alkylation of aromatic amines can be carried out in a fixed bed reactor with the reactants being fed downflow or upflow through the reactor. Alternately, the reaction can be carried out in a stirred autoclave. Although conversion of an aromatic amine to a ring alkylated aromatic amine product may be greater at temperatures near the upper end of the temperature range specified below, the degree of alkylation in the ortho-position, as opposed to the para-position, may be greatly reduced and olefin polymerization may occur.

Suitable temperatures for practicing the present invention range from about 50° to 425° C. The optimum temperature for operating the process will depend upon the driving force required to effect the alkylation reaction. For ethylene, that temperature will probably be greater than the reaction temperature required for propylene, the propylene temperature which will be greater than that for isobutylene.

Pressure has some effect on the selectivity to ortho-alkylated product but its effect is much less significant than temperature. Typical pressures used in the instant process range from atmospheric to about 5000 psia. Higher pressure is generally required for lower olefins such as ethylene wherein typical pressures range from 500 to 3000 psig while lower pressures ranging from 50 to 1500 psig are typically required for higher substituted olefins such as isobutylene.

Reaction time is an important factor in achieving high selectivity to the desired ortho-alkylated product as opposed to the para-alkylated product. Broadly, the reaction time can be expressed as liquid hourly space velocity (LHSV) of aromatic amine feed to the reactor and typical LHSV values range from 0.05 to about 6 hours$^{-1}$. When operating the alkylation process at relatively high temperatures, the LHSV should be increased somewhat in order to reduce reaction time as longer reaction times at high temperatures permit increased formation of the thermodynamically preferred para-product. In contrast, a lower LHSV value typically allows for higher conversion at lower temperatures wherein a lower reaction temperature permits ring alkylation at the ortho-position. Thus, by using a combination of an appropriate temperature range for a specific olefin and low LHSV one can obtain high conversion at high ortho to para ratios. These reaction conditions can be adjusted to favor production of the ortho-alkylated aromatic amine as opposed to the or N-alkylated or para-alkylated products.

The zeolites suitable for carrying out the ortho-alkylation of aromatic amines include both synthetic and naturally occurring zeolites including X, Y, K, and L zeolites, faujasite, mordenite, offretite, beta, omega, gmelinite, chabazite, clinoptilolite and the ZSM family comprising ZSM-4, ZSM-5, ZSM-11, ZSM-12, ZSM-21, ZSM-35 and ZSM-38. These zeolites may be further modified to enhance selectivity and reactivity. The preferred zeolite for practicing the present process is Y zeolite; e.g., LZ-Y82, manufactured by the Union Carbide Corporation, Tarrytown, N.Y.

The zeolites according to the present invention are porous materials comprising pores of generally uniform molecular dimension. Cavities or cages are formed in the zeolite and are connected by channels of generally defined diameter. For the practice of this invention, the cage diameter should be sufficiently large to permit the reactant molecules to effectively enter the interior of the zeolite for reaction and to exit as product. Typically, the pore diameter will range from about 6 to 15 Angstroms, but the required pore diameter can vary depending upon the alkylated aromatic amine product being produced.

An aromatic amine having an ethyl substituent can be prepared utilizing a zeolite having a smaller average pore diameter than can an aromatic amine having an tert-butyl or cyclohexyl substituent. Moreover, a mononuclear aromatic amine can be produced utilizing a zeolite having a smaller pore diameter than can a polynuclear aromatic amine. If the average pore diameter of the zeolite is too small or tortuous to permit entry of the reactants, conversion will be low at low temperatures and catalytic activity will be limited to surface catalysis. Higher temperatures may be required to enhance molecular diffusion as in the case of H-mordenite in propylene alkylation.

When initially prepared, the cation in a crystalline zeolite is typically an alkali metal such as sodium. The cation may be exchanged in sufficient proportion, generally in excess of 60%, with an acidic ion such as a rare earth metal, (e.g., lanthanum, cerium, praseodymium), a hydrogen atom or some of the transition metals such as nickel, copper, chromium, aluminum and the like for the practice of this invention. The substitution of various ions for the sodium ion alters the acidity of the zeolite thus making it more reactive and catalytically effective for ring alkylation of the aromatic amine. The process according to the present invention demonstrates high selectivity and conversion toward formation of ortho-alkylated aromatic amine products while also providing a higher rate of reaction than prior art processes.

In a preferred embodiment of the present invention, A process is disclosed for producing 2-isopropylaniline which comprises reacting aniline and propylene under conditions sufficient to effect an alkylation reaction, in the presence of a LZ-Y82 zeolite which has been thermally pretreated by heating the catalyst to a temperature greater than about 600° C. for a period ranging from 0.5 to about 10 hours while sweeping an inert gas over the heated catalyst to remove water and ammonia formed during the thermal treatment and subsequently recovering the 2-isopropylaniline.

The zeolites of the present invention are then subjected to a thermal treatment consisting of heating the zeolite to temperatures in excess of about 600° C. for a period ranging from 1 to about 10 hours while sweeping the catalyst bed with dry inert gas in order to remove water and ammonia formed during the thermal treatment. The pretreatment temperature and the temperature program used will depend on the particular zeolite and reactants being utilized. Some zeolites, when heated rapidly, lose a significant portion of their structure and, thus, must be heated carefully at a slow rate. An example of such a zeolite is the NH$_4$Y zeolite wherein a suitable heating profile is 2° C./minute until reaching the desired treatment temperature. The zeolite bed is then cooled and the process is conducted at the desired operating conditions.

The inert gases suitable for carrying out the thermal pretreatment step include argon, nitrogen, helium and any other gas which does not react with the zeolite under the conditions imposed during thermal pretreatment. The preferred inert gas is nitrogen.

The following examples are provided to further illustrate various embodiments of the invention and are not intended to restrict the scope of the invention.

EXAMPLE 1

Reaction of Aniline and Propylene over LZ-Y82 Zeolite

Several experimental runs were conducted by pre-drying HY zeolite (LZ-Y82 zeolite powder purchased from Union Carbide Corporation, Tarrytown, N.Y.) at various temperatures under a high flow of N$_2$. A fresh catalyst bed of about 6 gm of LZ-Y82 was used for each run. A preheating zone containing 14 ml vycor glass chips was also provided in the reaction tube. Both the catalyst as well as the vycor glass chips were of 12/18 mesh particle size. The reactor tube was 316 stainless steel with an internal diameter of 0.31 inches. End run was conducted at about 250° C. and 900 psia using an aniline to propylene molar ratio of 0.2/1. Aniline was predried over a 3A molecular sieve prior to reaction. Details pertaining to each run are provided below.

RUN 1

The catalyst bed was not subjected to a thermal pretreatment. The reactor was purged with $N_2$ at room temperature and aniline was introduced. Upon the reactor reaching the desired pressure, the reactor temperature was increased to 50° C. and propylene was introduced. Aniline/propylene feed mole ratio was 0.2 and aniline was introduced at a LHSV of 0.5 hr$^{-1}$. The reactor was then heated to 250° C. The total ortho-selectivity, defined as the sum of 2-isopropylaniline and 2,6-diisopropylaniline, was about 68.3%.

RUN 2

The catalyst bed was heated at a rate of 2° C./min. to 250° C. and was held at this temperature for two hours and then further heated to 400° C. at a rate of 2° C./min. The catalyst bed was maintained at 400° C. for ten hours and then cooled to room temperature under a nitrogen atmosphere. The flow rate of $N_2$ during calcination through the reactor bed was about 1080 standard cc/min. The cooled reactor was brought on stream as in Run 1.

RUN 3

The catalyst bed was heated to 250° C. according to the procedure in Run 2 followed by heating to 502° C. at a rate of 2° C./min. whereby the catalyst bed was held at that temperature for three hours, and then cooled to room temperature.

RUN 4

The catalyst bed was pretreated up to 502° C. as in Run 3, and was further heated to 570° C. at a rate of 0.2° C./min. The bed was held at 570° C. for two hours prior to cooling to room temperature.

RUN 5

The catalyst bed was heated to 570° C. according to Run 4. Thereafter, the bed was further heated at a rate of 0.2° C./min. to 628° C., held at 62° C. for 2.5 hours, and then cooled to room temperature.

RUN 6

The catalyst bed was heated to 628° C. according to Run 5. Thereafter, the bed was heated to 650° C. at a rate of 0.2° C./min., further heated to 690° C. at a rate of 2° C./min., held at that temperature for two hours, and then cooled to room temperature.

RUN 7

The catalyst bed was heated to 690° C. according to Run 6. Thereafter, the bed was heated at a rate of 2° C./min. to 775° C. and held at that temperature for two hours before cooling it to room temperature.

The results achieved by the zeolites which were subjected to thermal pretreatment according to Example 1 are provided in Table 1 wherein reaction selectivity, aniline conversion and relative rate, R, for Runs 1 through 7 is presented. The relative rate, R, is presented in order to normalize for variation in aniline conversion as the pretreatment temperature was changed. R is calculated by the equation:

$$\text{Relative Rate } R = \frac{[LHSV \ln(1 - X)] \text{ thermally pretreated}}{[LHSV \ln(1 - X)] \text{ not thermally pretreated}}$$

wherein X represents the fractional conversion of aniline. The use of the above-mentioned equation provides a good approximation of the relative rates because all of the conversion data are within a narrow band.

Table 1 demonstrates that more than a threefold increase in relative rate is achieved for the alkylation of aniline when the zeolite is thermally pretreated at a temperature greater than 600° C. under the conditions enumerated herein. Moreover, this increased activity is accompanied by an increase in total ortho selectivity. For example, overall ortho selectivity increases from 68.3% for the catalyst prior to thermal pretreatment (Run 1) to about 77% for the catalyst thermally pretreated at 775° C. (Run 7). Finally, the selectivity to the undesirable 4-isopropylaniline is reduced from 3.3 (Run 1) to 2.4 (Run 7).

TABLE 1

Data Points for Example 1
Aniline/Propylene Feed Mole Ratio = 0.2/1

| | RUN # | | | | | | |
|---|---|---|---|---|---|---|---|
| | 1 | 2 | 3 | 4 | 5 | 6 | 7 |
| Pretreatment Temperature (°C.) | No | 400 | 502 | 570 | 628 | 691 | 775 |
| Aniline Conversion (%) | 60 | 65.9 | 57.5 | 57.0 | 58.3 | 56.4 | 61.4 |
| Selectivity (%) | | | | | | | |
| 2-isopropylaniline | 51.0 | 48.0 | 55.6 | 57.5 | 58.5 | 59.1 | 57.7 |
| 2,6-diisopropylaniline | 17.3 | 20.9 | 16.0 | 16.2 | 17.2 | 16.1 | 19.3 |
| N-isopropylaniline | 19.4 | 17.2 | 17.2 | 15.7 | 13.9 | 15.0 | 12.4 |
| 4-isopropylaniline | 3.3 | 3.2 | 3.3 | 2.9 | 2.7 | 2.5 | 2.4 |
| N,2-diisopropylaniline | 5.0 | 5.7 | 4.4 | 4.5 | 4.5 | 4.6 | 4.8 |
| 2,4,6-triisopropylaniline | 0.4 | 0.5 | 0.2 | 0.4 | 0.4 | 0.4 | 0.5 |
| LHSV* (h$^{-1}$) | 0.5 | 0.5 | 1.0 | 1.5 | 1.8 | 1.6 | 1.6 |
| Temperature (°C.) | 250.6 | 251.6 | 249.4 | 249.8 | 250 | 250 | 250.5 |
| Pressure (psia) | 888 | 914 | 850 | 929 | 875 | 899 | 894 |
| Relative Rate R (Equation 1) | 1 | 1.2 | 1.9 | 2.7 | 3.4 | 2.9 | 3.3 |

*LHSV is defined on the basis of aniline flow rate at room temperature, i.e.:

$$LHSV = \frac{\text{volumetric flow rate of aniline (cc/h)}}{\text{volume of catalyst bed}}$$

EXAMPLE 2

Reaction of Aniline and Propylene over LZ-Y62 Zeolite

A NaNH$_4$Y zeolite (LZ-Y62 zeolite powder purchased from Union Carbide, Tarrytown, N.Y.) was placed in a furnace purged with dry N$_2$. The catalyst was heated to 400° C. at 2° C./min. and was maintained at 400° C. for four hours prior to being cooled to room temperature. Subsequently, the catalyst was exposed to 55% relative humidity. Thereafter the sodium cations of the zeolite were exchanged with ammonium cations by refluxing the zeolite in a 1M NH$_4$NO$_3$ solution.

Three runs were made on the material prepared above. In each run, the catalyst was activated to 400° C., 600° C. and 750° C. under a flow of helium utilizing the procedure described in Example 1. The relative rates for the reaction of aniline and propylene for Example 2, as calculated according to the equation above, are presented in Table 2. Table 2 demonstrates that the total ortho selectivity increases with an increase in thermal pretreatment temperature and reaches 82% for the catalyst which was thermally pretreated at 750° C. (Run 10).

TABLE 2

Results for Example 2 - Aniline/Propylene Reaction
(Aniline/Propylene Feed Molar Ratio = 0.2,
T = 250° C., P = 900 psia)

| Run | Pretreatment Temperature (°C.) | Total Ortho-Selectivity (%) | Relative Rate R (Equation 1) |
|---|---|---|---|
| 8 | 400 | 70 | 1.0 |
| 9 | 600 | 76 | 3.4 |
| 10 | 750 | 82 | 1.0 |

The process according to the present invention solves the handling and reactivity problems associated with some commercial homogeneous catalysts currently utilized for the alkylation of aromatic amines. Moreover, the thermally activated zeolites according to the present invention provide improved product selectivity toward the desired ortho alkylated aromatic amines combined with improved reaction rates.

Having thus described the present invention, what is now deemed appropriate for Letters Patent is set forth in the following appended claims.

We claim:

1. A process for producing an alkylated aromatic amine which comprises: reacting an aromatic amine having at least one hydrogen atom ortho to the amine functionality and an olefin under conditions sufficient to effect an alkylation reaction in the presence of an ammonium exchanged Y zeolite catalyst which has been thermally pretreated by heating the catalyst to a temperature greater than about 600° C. for a period ranging from 1 to 10 hours while sweeping an inert gas over the heated catalyst to remove water and ammonia formed during the thermal treatment and recovering the alkylated aromatic amine.

2. The process according to claim 1 wherein the aromatic amine is represented by the formula:

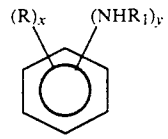

wherein R is selected from a hydrogen atom, a linear or branched alkyl having from 1 to about 10 carbon atoms, a halogen, phenol, alkoxy, ester or nitrile; R$_1$ is selected from a hydrogen atom or a linear or branched alkyl group having from 1 to about 10 carbon atoms; x is 1 or 2 and y is 1 or 2.

3. The process according to claim 2 wherein the aromatic amine is selected from aniline, toluidine, xylidene, toluenediamine, xylidenediamine, diphenylamine, N-ethylaniline, N-propylaniline, n-propylamino-amino toluene, isobutylaniline, phenylaniline, or phenylenediamine.

4. The process according to claim 3 wherein the olefin is selected from a linear or branched acyclic or cyclic olefin having from 2 to about 8 carbon atoms.

5. The process according to claim 4 wherein the olefin is selected from ethylene, propylene, butene, isobutylene, isoamylene, cyclohexene or 1-methylcyclohexene.

6. The process according to claim 5 wherein the mole ratio of olefin to aromatic amine ranges from 1 to about 20 moles olefin per mole of aromatic amine.

7. The process according to claim 6 wherein the mole ratio of olefin to aromatic amine ranges from 2 to about 10 moles olefin per mole of aromatic amine.

8. The process according to claim 7 wherein the reaction temperature ranges from 50° C. to about 425° C. and the pressure ranges from atmospheric to about 5000 psia.

9. The process according to claim 8 wherein liquid hourly space velocity of aromatic amine feed ranges from 0.05 to about 6 hours$^{-1}$.

10. A process for producing 2-isopropylaniline which comprises: reacting aniline and propylene under conditions sufficient to effect an alkylation reaction in the presence of an ammonium exchanged Y-zeolite catalyst which has been thermally pretreated by heating the catalyst to a temperature greater than about 600° C. for a period ranging from 0.5 to about 10 hours while sweeping an inert gas over the heated catalyst to remove water and ammonia formed during the thermal treatment and subsequently recovering the 2-isopropylaniline.

11. The process according to claim 10 wherein the Y-zeolite is LZ-Y82.

12. The process according to claim 11 wherein the reaction temperature ranges from 50° C. to about 425° C. and the pressure ranges from atmospheric to about 5000 psia.

13. The process according to claim 12 wherein liquid hourly space velocity of aromatic amine feed ranges from 0.05 to about 6 hours$^{-1}$.

14. The process according to claim 1 wherein the ammonium exchanged Y zeolite is LZ-Y62.

15. The process according to claim 10 wherein the ammonium exchanged Y zeolite is LZ-Y62.

* * * * *

UNITED STATES PATENT AND TRADEMARK OFFICE
CERTIFICATE OF CORRECTION

PATENT NO.   :   5,026,912

DATED        :   June 25, 1991

INVENTOR(S)  :   Agrawal et al.

It is certified that error appears in the above-identified patent and that said Letters Patent is hereby corrected as shown below:

Column 6, line 29, delete "Jected" and insert -- jected --.

Column 7, line 43, delete "62°" and insert -- 628° --.

Column 8, line 15, delete "Jected" and insert -- jected --.

Signed and Sealed this

Tenth Day of November, 1992

Attest:

DOUGLAS B. COMER

*Attesting Officer*    *Acting Commissioner of Patents and Trademarks*